United States Patent
Huxel et al.

[11] Patent Number: 6,001,117
[45] Date of Patent: Dec. 14, 1999

[54] BELLOWS MEDICAL CONSTRUCT AND APPARATUS AND METHOD FOR USING SAME

[75] Inventors: Shawn Thayer Huxel, Lakehurst; Kevin Leonard Cooper, Warren; Jie Jenny Yuan, Bridgewater; Murty Narayan Vyakarnam, Edison, all of N.J.

[73] Assignee: Indigo Medical, Inc., Cincinnati, Ohio

[21] Appl. No.: 09/044,614

[22] Filed: Mar. 19, 1998

[51] Int. Cl.⁶ ............................................. A61B 17/00
[52] U.S. Cl. .................................................. 606/191
[58] Field of Search .................................. 606/191–200, 606/108, 153–155; 623/1, 12, 11; 604/8; 128/898, 899

[56] References Cited

U.S. PATENT DOCUMENTS

| | | | |
|---|---|---|---|
| 5,015,253 | 5/1991 | MacGregor | 623/1 |
| 5,059,211 | 10/1991 | Stack et al. | 606/198 |
| 5,085,629 | 2/1992 | Goldberg et al. | 604/8 |
| 5,147,385 | 9/1992 | Beck et al. | 623/1 |
| 5,160,341 | 11/1992 | Brenneman et al. | 606/198 |
| 5,171,262 | 12/1992 | MacGregor | 623/1 |
| 5,192,289 | 3/1993 | Jessen | 606/155 |
| 5,246,445 | 9/1993 | Yachia et al. | 606/108 |
| 5,419,760 | 5/1995 | Narciso, Jr. | 604/8 |
| 5,423,885 | 6/1995 | Williams | 623/1 |
| 5,443,458 | 8/1995 | Eury | 604/891.1 |
| 5,500,013 | 3/1996 | Buscemi et al. | 623/1 |
| 5,527,337 | 6/1996 | Stack et al. | 606/198 |
| 5,551,954 | 9/1996 | Buscemi et al. | 623/1 |
| 5,593,434 | 1/1997 | Williams | 623/1 |
| 5,599,291 | 2/1997 | Balbierz et al. | 604/8 |
| 5,599,492 | 2/1997 | Engleson | 264/167 |
| 5,618,298 | 4/1997 | Simon | 606/194 |
| 5,662,616 | 9/1997 | Bousquet | 604/175 |
| 5,662,700 | 9/1997 | Lazarus | 606/108 X |
| 5,695,474 | 12/1997 | Daugherty | 606/162 |

FOREIGN PATENT DOCUMENTS

| | | | |
|---|---|---|---|
| 0 183 372 A1 | 6/1986 | European Pat. Off. | A61M 29/00 |
| 0 528 039 A1 | 2/1993 | European Pat. Off. | A61L 27/00 |
| 0 604 022 A1 | 6/1994 | European Pat. Off. | A61F 2/06 |
| 0 689 807 A2 | 6/1994 | European Pat. Off. | A61F 2/06 |
| 0 634 152 A1 | 1/1995 | European Pat. Off. | A61F 2/06 |
| WO 90/04982 | 5/1990 | WIPO | A61L 27/00 |
| WO 93/15787 | 8/1993 | WIPO | A61M 29/00 |
| WO 94/05364 | 3/1994 | WIPO | A61M 29/00 |
| WO 95/26762 | 10/1995 | WIPO | A61L 31/00 |
| WO 96/11720 | 4/1996 | WIPO | A61M 29/00 |

*Primary Examiner*—Michael Buiz
*Assistant Examiner*—Vikki Trinh

[57] ABSTRACT

A medical construct particularly useful as a stent, comprising an axially compressible bellows of a material and dimensions sufficient to provide negligible resistance to flexure transverse to the axis and negligible recoil under compression or expansion along the axis, and apparatus and a method for deploying the same.

4 Claims, 5 Drawing Sheets

BELLOWS MEDICAL CONSTRUCT AND APPARATUS AND METHOD FOR USING SAME

FIELD OF THE INVENTION

This invention relates to a medical construct useful as a stent, among other things, and more specifically, biocompatible, absorbable polymer medical constructs; for opening occlusions and maintaining patency in body lumens or for providing flow out of or between parts of a living body.

BACKGROUND OF THE INVENTION

Metallic stenting, especially in cardiovascular angioplasty, has become important in simplifying surgical procedures and reducing patient hospital stays. Most significantly, stenting has dramatically reduced restonosis.

Several issues, however, still remain for metallic based stents. These include thrombogenicity and persistence of restonosis in some patients, poor capabilities to deliver drugs, and damage to the lumen during expansion. Furthermore, in some instances, such as stenting of the urethra after surgical intervention for benign prostate hypertrophy (BPH) to prevent post-operative urinary retention, it would be highly desirable to have a stent formed from a polymer which keeps the lumen open until swelling has subsided, then is passed in the urine stream.

One potential method to overcome these challenges is to provide an absorbable stent which is engineered with the proper strength and stiffness to resist the hydrostatic, axial and compressive loads in a tubular vessel (e.g., urethra), but not over-engineered to cause tissue damage, as in the case of metals, can be expanded to conform to the organ's vessel walls, and can deliver drugs to specific sites, both in the lumen and in the body fluids (e.g., urine, bile). In addition, the device should maintain the advantages of metallic stents such as flexibility for ease in delivery, thinness in its walls so as to not disrupt fluid flow, radio-opaqueness for post-operative management, and support for the organ's vessel wall until healing has occurred.

Several patents describe absorbable stents to overcome the disadvantages of metallic stenting. However, these either require the use of a balloon catheter to expand them, and/or are not sufficiently flexible in any direction transverse to their longitudinal axis. Examples of such stents, along with their use of pores to allow tissue ingrowth, are shown in, e.g., U.S. Pat. Nos. 5,059,211; 5,171,262; 5,551,954; and European Patent Application 183,372.

Yet another approach is to use a resorbable or non-resorbable coil spring stent that is collapsed within or on an insertion device for insertion into, e.g., a urethra, but which when ejected from the insertion device automatically expands. Such a stent does not need the use of a balloon catheter. However, insertion and placement within the urethra occurs while the stent is confined within or on an insertion device. Such a requirement can reduce flexibility transverse to the longitudinal axis, because of that insertion device. As a result, the placement of the stent might not easily accommodate sharp turns in the body lumen in which the stent is being placed. Examples of such stents include those shown in U.S. Pat. Nos. 5,160,341 and 5,246,445.

Therefore, what has been needed prior to this invention is a device which is flexible during delivery and deployment so as to ensure easy pass through long tortuous paths and will expand to match the diameter of the tissue lumen, and additionally, dramatically increases in radial stiffness after deployment to resist hydrostatic and compressive pressures.

SUMMARY OF THE INVENTION

In accordance with one aspect of the invention, there is provided a tubular construct for insertion into a body lumen to open occlusions or to provide flow out of or between parts of a living body, the construct comprising:

an elongated flexible tube with opposite ends, the tube having a central axis extending along its length;

a portion of the tube between the ends comprising collapsible bellows, the bellows being constructed of a material and dimensions sufficient to provide negligible resistance to flexure transverse to the axis and negligible recoil under compression or expansion along the axis;

so that the construct is easily flexed at the bellows to negotiate turns in the body lumen, and is expandable under axial compression at the bellows from a relatively narrow diameter configuration transverse to the axis, to a relatively wide diameter configuration which is retained when the axial compression force is released.

In accordance with another aspect of the invention, there is provided an apparatus for opening occlusions in a body lumen or to provide flow out of or between parts of a living body, comprising:

a tubular construct comprising an elongated flexible tube with opposite ends, the tube having a central axis extending along its length, a portion of the tube between the ends comprising collapsible bellows, the bellows being constructed of a material and dimensions sufficient to provide negligible resistance to flexure transverse to the axis and negligible recoil under compression along the axis, so that the construct is easily flexed at the bellows to negotiate turns in the body, and is expandable under axial compression at the bellows from a relatively narrow diameter configuration transverse to the axis, to a relatively wide diameter configuration which is retained when the axial compression force is released; and an applicator for inserting, guiding, and deploying the construct within the body.

In accordance with another aspect of the invention, there is provided a method of delivering and deploying a tubular construct into a body lumen to open occlusions or to provide flow therein, comprising the steps of:

a) inserting a tubular construct comprising a flexible and axially collapsible bellows of a diameter sufficiently less than that of the lumen when axially uncompressed, and greater when axially compressed, into the lumen;

b) advancing the construct through the lumen and around any bends therein to a desired site of deployment; and c) axially compressing at least the bellows of the construct until the bellows achieves a diameter approximately equal to that of the lumen site, so as to be retained at the lumen site.

Accordingly, it is an advantageous feature of the invention that an axially compressive corrugated stent is provided that overcomes the radial deficiency of absorbable stents of the prior art and the insufficiency described above for metallic stents, while maintaining the advantages of both.

It is another advantageous feature of the invention that such a stent and a method of use are provided that give enough flexibility to allow the surgeon to pass it through a lumen having a tortuous path (e.g., urethra).

Yet another advantageous feature of the invention is that a balloon catheter or other mechanical assistance is not required to expand the stent to the desired shape and diameter. By simply axially compressing the stent to form the expanded diameter, it presses against the tissue lumen to open the vessel and maintain patency. In addition, when the stent of the present invention is in the compressed state, its radial stiffness is dramatically increased proportional to its increased mass moment of inertia.

BRIEF DESCRIPTION OF THE DRAWINGS

FIG. 3C is a view similar to that of FIG. 3B but showing the applicator being withdrawn;

DESCRIPTION OF THE PREFERRED EMBODIMENTS

The invention is described herein with respect to certain preferred embodiments, in which a stent is applied post-surgically to a body lumen such as a urethra, using a cystoscope or a catheter (but not a balloon catheter). In addition, the invention is applicable to a bellows construct applied in place of or before surgery, into lumens other than urethras, by insertion devices other than catheters or cystoscopes, and indeed for uses in a living body other than as a stent.

Figure 2:
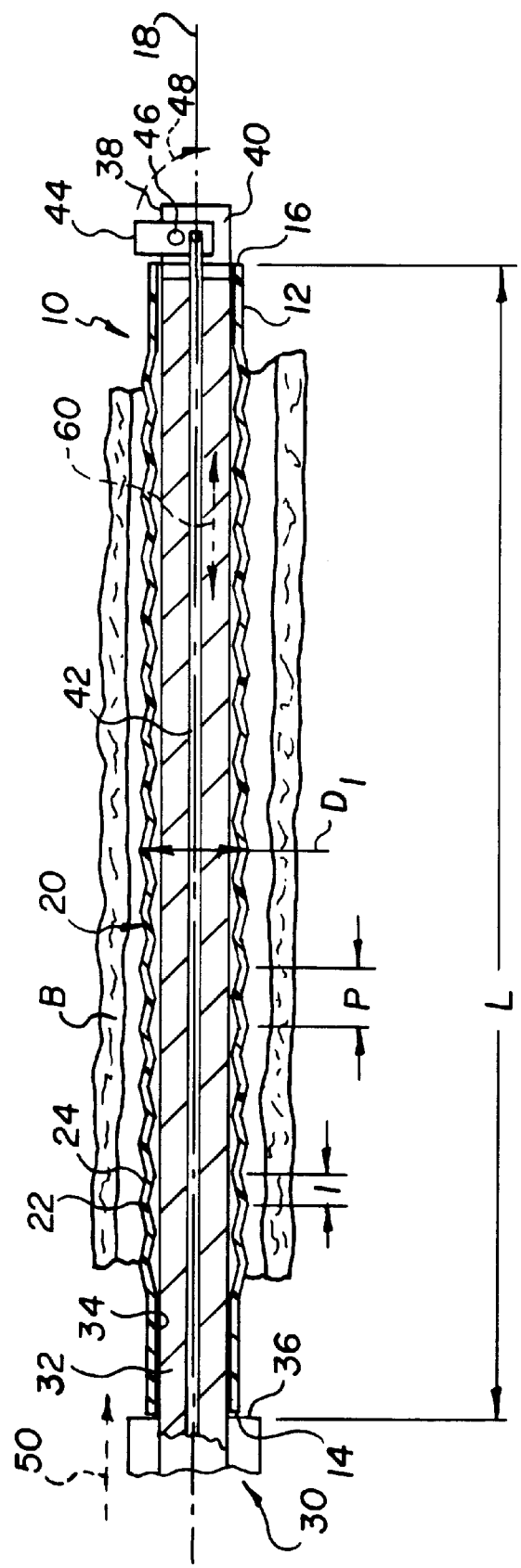
FIG. 2 is a fragmentary axial sectional view taken generally along the plane II—II of FIG. 1, in which the body lumen is shown added at the intended site of deployment.

As used herein, "bellows" refers to the alterable shape achieved by repeated corrugations extending around the complete circumference of the tube with a pitch "P", FIG. 2, before compression, measured between peaks of the corrugations, and the fact that such corrugations are capable of compression and expansion towards and away from each other. It does not refer to a function of drawing in or expelling a fluid by expansion or compression of the corrugations, since that in fact is not its use. Nor for that matter does it refer to multiple cycles of compression and expansion as that also is not a feature of its use.

As used herein, "flexure transverse to said axis" means at a significant angle to the axis, including but not limited to, 90° to the axis. It is such a flexure that the stent must undergo while being advanced through a body lumen and around variously angled turns. Hence, its resistance is substantially negligible.

Also, as used herein, "negligible resistance to flexure" means, when measured using a method shown in FIG. 4, described below, a resistance no greater than about 2 Newtons of force (0.4 pounds) in an exactly perpendicular direction to the axis, per cm of travel per 2.5 cm of length.

"Negligible recoil under compression" means, when closed by any force, the bellows remains closed with essentially zero spring-back. Force is required to return it to the original configuration.

Figure 1:
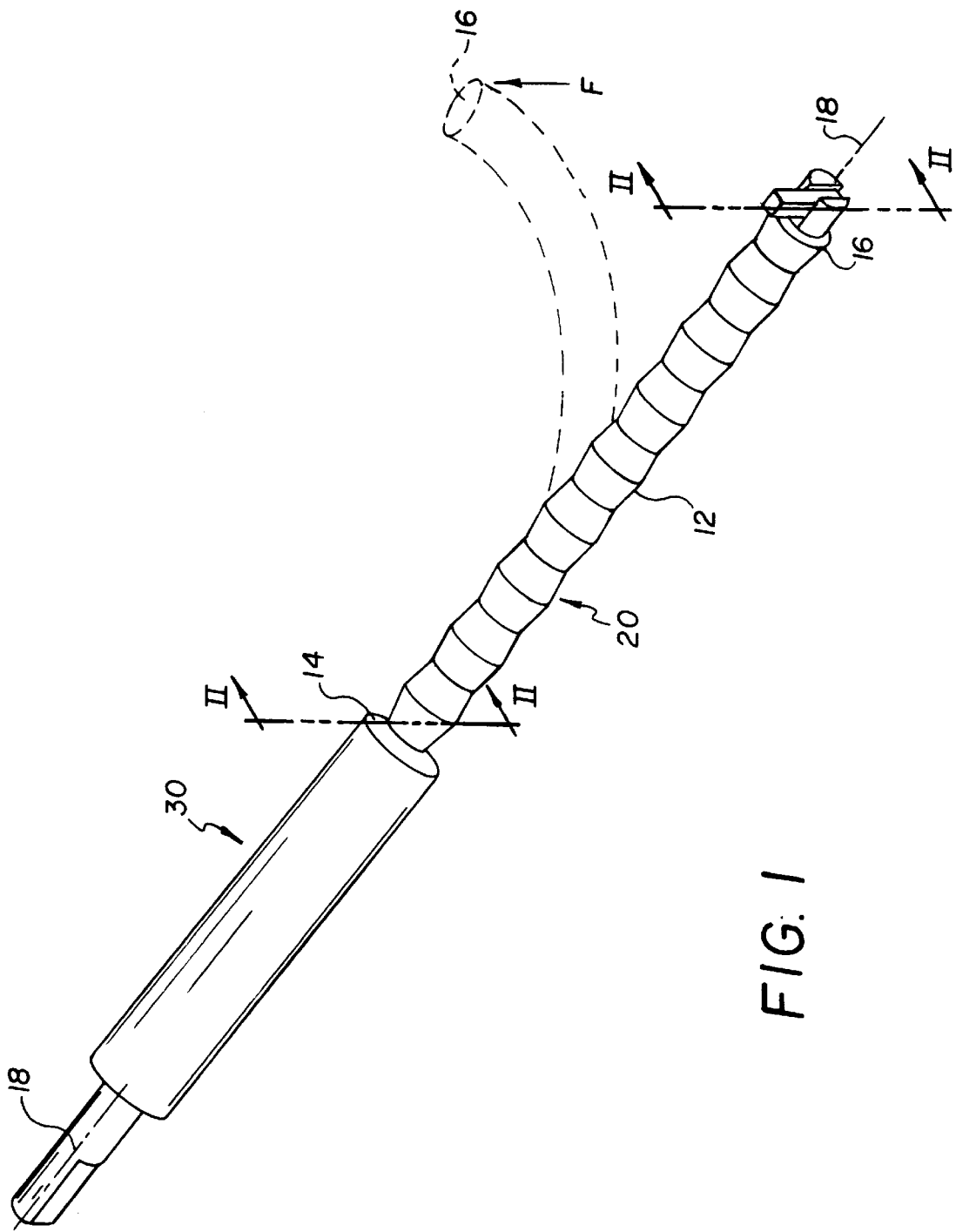
FIG. 1 is a fragmentary isometric view of an embodiment of the invention on an applicator, ready for insertion into a lumen.

In accord with one aspect of the invention, the construct 10, FIGS. 1-2, comprises an elongated flexible tube 12 of a biocompatible, biodegradable polymer, the tube having a total length L between opposite ends 14 and 16 and a longitudinal axis 18, FIG. 2, extending between the ends. A portion of the tube, indeed preferably at least 50% of its length, comprises a bellows 20 formed by repeated corrugations having a pitch "P", the length of the pitch varying with the intended use of the construct. When tube 12 is uncompressed, it has a relatively narrow outside diameter "$D_1$" that the bellows that is easily accommodated within a body lumen "B".

Bellows 20 in turn comprises a series of conical sections joined back to back so that a ridge 22 is formed spaced from the next ridge by a groove 24. The axial distance between a ridge and its groove defines a distance "l" which, of course, is one-half the pitch "P" in FIG. 2.

For use as a stent in a urethra, useful dimensions for construct 10 are as follows:

L=150 mm $D_1$=from 1 mm to 50 mm

P=0.1 mm to about 5 mm l=0.05 mm to about 2.5 mm

The thickness of the wall of tube 12, in such cases, would be from about 0.04 mm to about 2 mm.

For insertion of the construct into lumen B, it is preferably mounted on an applicator 30. A variety of applicators are useful, for example, a cystoscope or a catheter. As shown in FIGS. 1 and 2, applicator 30 comprises a cystoscope, and in particular one in which a hollow tube 32 with a longitudinal bore 34, that extends outwardly from a stiff sleeve 36, tube 32 having a distal end 38 which has a groove 40 extending transversely to bore 34. A control wire 42 freely extends through bore 34 to end 38, where it is pinned to a pivotal finger 44 pivoted at 46 to rotate, arrow 48, from a position transverse to bore 34 and in contact with end 16 of construct 10, to a position aligned with axis 18 and not in contact with construct 10, FIG. 3B.

Useful polymers for the manufacture of construct 10 comprise bio-absorbable aliphatic polyesters, especially those formed from lactone monomers in a conventional manner. Suitable lactone monomers may be selected from the group consisting of glycolide, lactide (l, d, dl, meso), p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2one, 1,5-dioxepan-2-one, 1,4-dioxan-2-one, 6,8-dioxabicycloctane-7-one and combinations of two or more thereof. Preferred lactone monomers are selected from the group consisting of glycolide, lactide, trimethylene carbonate, ∈-caprolactone and p-dioxanone.

Thus the preferred polymers are polyesters selected from the group consisting of poly(lactide), poly(glycolide), poly(∈-caprolactone), poly(p-dioxanone), poly(trimethylene carbonate), copolymers and blends thereof.

Alternatively, the polymer can be a nonabsorbable biocompatible polymer selected from the group consisting of poly(propylene), poly(ethylene), poly(alkyleneoxide), thermoplastic elastomers, nylon, polyurethane, polyester, hydrogels, a flouropolymer, and copolymers and blends thereof. Such polymers are useful when the construct is intended to be permanent. Therapeutic agents can still be delivered by such polymers, by coating them on the outside of the construct, or by having them be leached out by water, especially if the polymer is water-swellable.

The construct of the present invention is formed from such polymers by use of various injection and extrusion molding equipment equipped with dry nitrogen atmospheric chamber(s) at temperatures and residence times to sufficiently form the structure of the bellows of the present invention.

The corrugated structure of the bellows is formed by a process in which the extruded thin-walled polymer tube is cut into the desired lengths. These tubes are then placed on a mandrel which has grooves. The tube is then cold stretched and formed into the grooved shape by using a rotating head which forces the tube wall into the depressions on the mandrel. The formed tube is then held in the compressed state for a certain time so that the polymer relaxes and stays in shape. The depth and the angle of these depressions are the critical design factors in the ability of the corrugated tube to function as desired.

The corrugated structure can also be formed by a one-step process in which the hot extrudate from an extruder is fed directly into a vacuum forming process, wherein the die head of the extruder extends into the closed area of revolving mold-block halves. A combination of air pressure inside the tube and the use of an external vacuum forces the hot plastic to form into the shape of the mold block. The corrugated tube is then cooled and wrapped or cut into given lengths.

Furthermore, bellows 20 can be perforated with various apertures for tissue ingrowth. Selective annealing of cross-sections of the device of the present invention can be used to stiffen the structure.

Additionally, the polymers of construct 10 can be used as a drug delivery matrix. To form this matrix, the polymer is mixed with a therapeutic agent. The variety of different therapeutic agents which can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents, antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradoil and other steroids, including corticosteroids; hypnotics; immunosuppressives; muscle relaxants; parasympatholytics; psychostimulants; sedatives; and tranquilizers; and naturally derived or genetically engineered proteins, polysaccharides, glucoproteins, lipoproteins, or thrombogenetic and restenoic reducing agents.

Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.0010% to about 70%, more typically about 0.001% to about 50%, most typically about 0.001% to about 20% by weight of the matrix.

The quantity and type of polymer incorporated into the drug delivery matrix will vary depending on the release profile desired and the amount of drug employed.

Importantly, such a construct 10, because of the bellows 20, has a negligible resistance to flexure transverse to axis 18, FIG. 1. That is, if the construct 10 alone, without the applicator, is subjected to a force F (as per the arrow), it takes only 0.9 Newtons of force to push end 16 1 cm away from axis 18, because of the corrugations. This is the familiar "bendable straw" phenomenon that is conventionally used with drinking straws.

Figure 4:
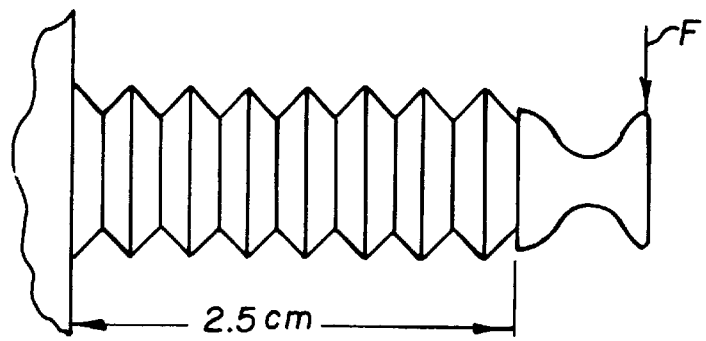
FIG. 4 is a fragmentary, partially schematic elevational view depicting a test configuration.

This test is done in the manner shown in FIG. 4. That is, a test device 2.5 cm in length, such as the tubular construct of the invention or any other, is epoxied to a fixed support at one end, and if the device is an open tube, a thumb tack is epoxied at the other end. The force F is applied as shown to determine how much is needed to bend it perpendicularly, one cm.

In contrast, a control comprising a straight tube otherwise of the same dimensions and material, required at least 18 Newtons of force to push it one cm.

In use, FIGS. 2, 3A, 3B, and 3C, the construct 10 and its applicator 30 are inserted into body lumen B, FIG. 2, and advanced to a desired site of deployment, for example, a site of occlusion or potential occlusion Then, bellows 20 is axially compressed by the operator pushing sleeve 36 along tube 32, arrow 50, to force relative movement between distal end 16 of construct 10 and proximal end 14. This in turn, FIG. 3A, causes the bellows 20 to expand radially, preferably to take on an outside diameter $D_2$, FIG. 5, that is approximately equal to the inside diameter of lumen B. For the urethral example noted above, a useful value for $D_2$ is about 10 mm, for a D1 value of 6 mm in FIG. 2. Pitch "P" is then reduced from an initial value of about 5 mm to about 2 mm.

Optionally, in the event the operator wishes to deploy construct 10 so that ridges 22, FIG. 2, do not scrape the interior of lumen B, the stent can be deployed while inside a smooth protective sleeve of the applicator (not shown).

Figure 3A:
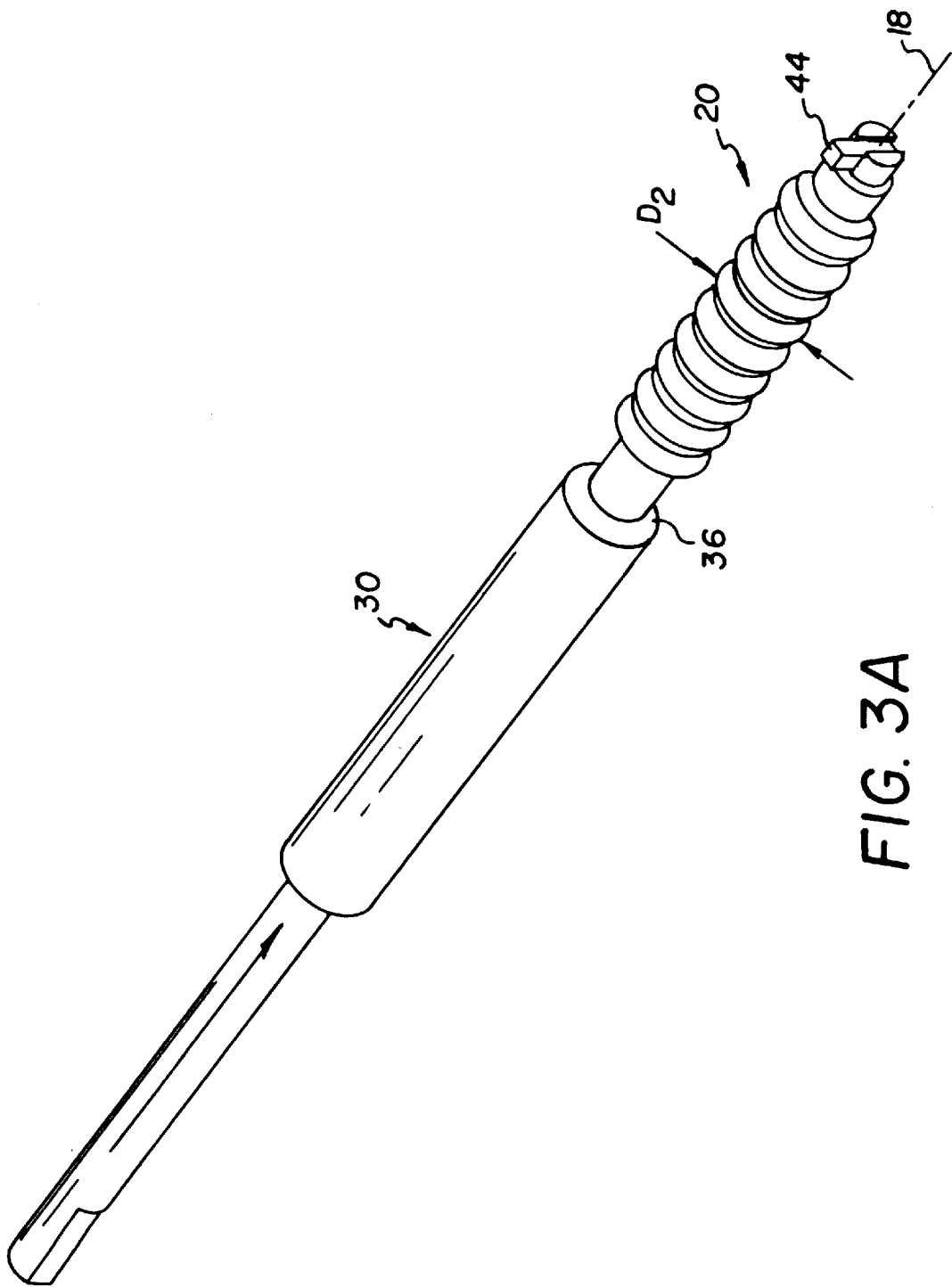
FIG. 3A is a view similar to that of FIG. 1, except showing the stent in place at the site of FIG. 2 and compressed for deployment.
Figure 3B:
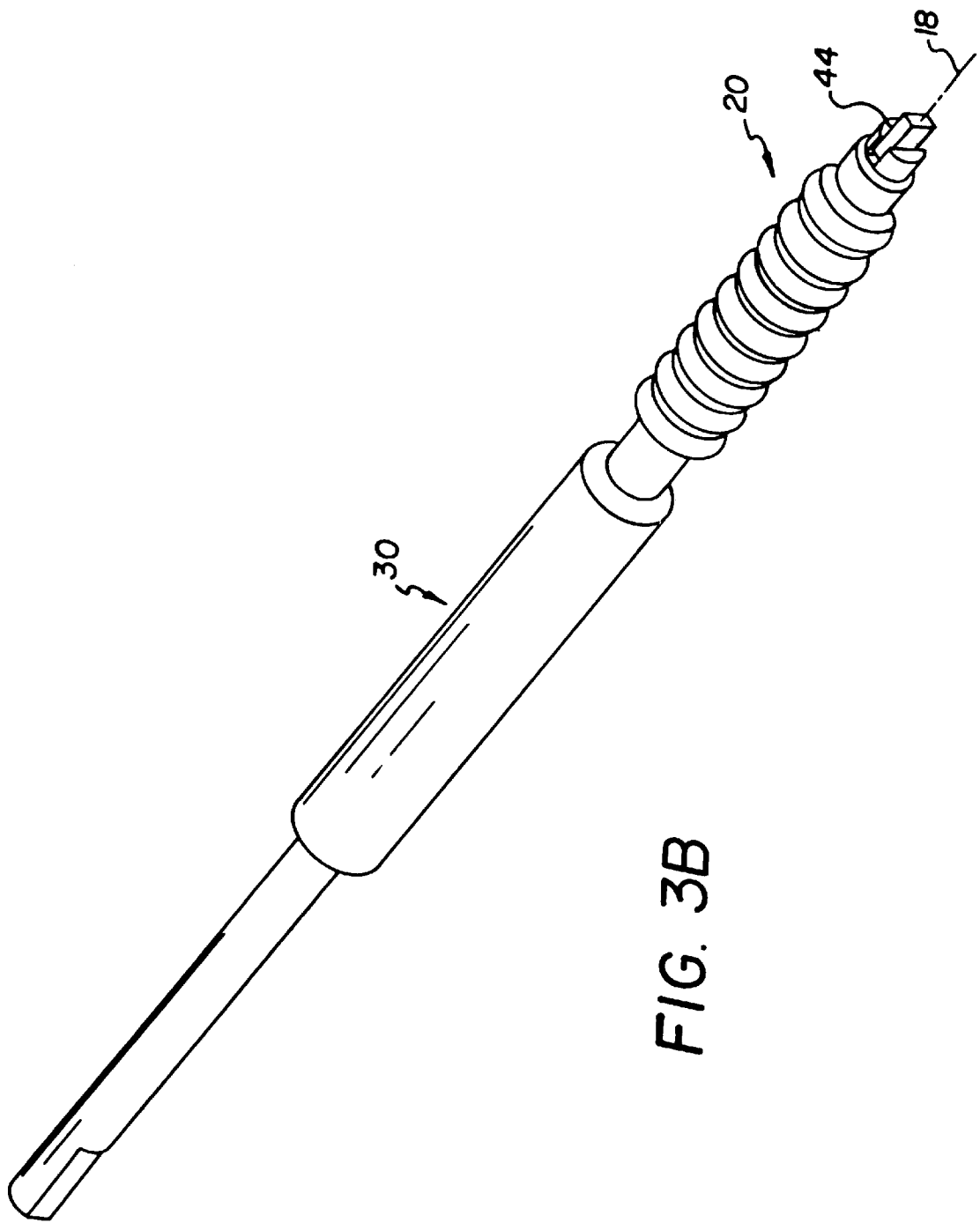
FIG. 3B is a view similar to that of FIG. 3A, showing the next step in the deployment.

Once at the site, FIG. 2, finger 44 is pivoted downward to align with axis 18, FIG. 3B, so that applicator tube 32 can be pulled out the interior of stent 10, arrow 60, FIG. 2, and applicator 30 withdrawn entirely.

Figure 5:
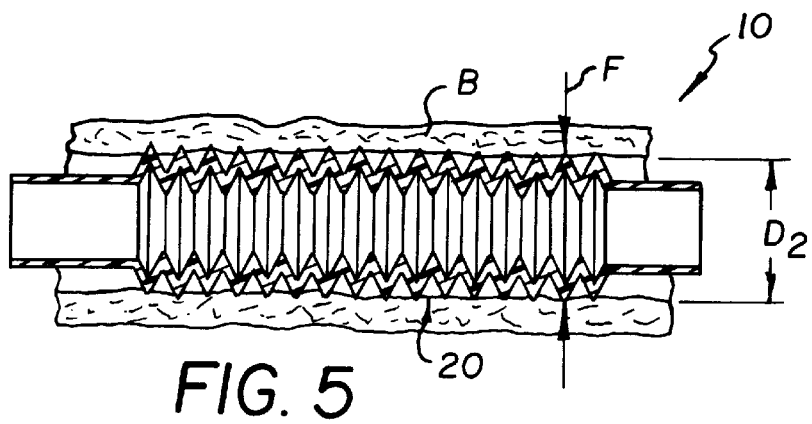
FIG. 5 is a sectional view similar to that of FIG. 2 but showing the stent fully deployed.

When construct 10 is in its diameter-expanded form, FIGS. 3C and 5, the bellows provides a high degree of compressive stiffness as well as negligible recoil of expansion or compression. That is, when axially compressed, there is substantially no resilience such as would cause the bellows to return to its axially uncompressed form. This, of course, is important in retaining the construct in the configurations shown in FIG. 5.

The compressive strength of the construct 10 having the dimensions noted above, is approximately 40 Newtons per cm length, when tested with a compressive force F, FIG. 5.

Figure 6:
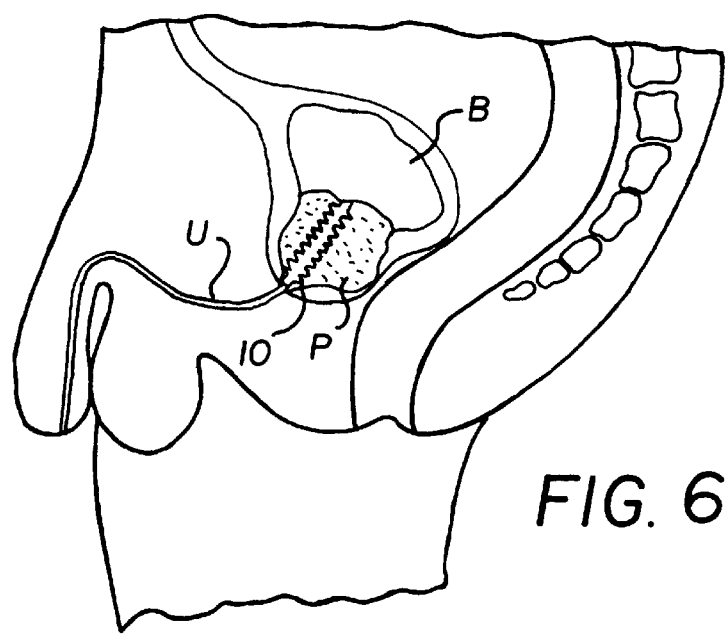
FIG. 6 is a fragmentary, simplified cross-sectional view of a male pelvis with the stent of the invention in place.

FIG. 6 illustrates construct 10 deployed in its axially compressed state in the portion of the urethra "U" that extends through the prostate P to the bladder B, alleviating occlusion due to the prostate. It is positioned there by access through the urethra, as is conventional.

In addition, pores, slits or other openings can be incorporated into the inner or outer surface or through the entire tube for increased tissue growth or cell seeding. This would be especially important for nerve guides and vascular grafts. Such pores are formed by extraction of salts from the formed device, by laser cutting, lyophilization or super critical fluid (SCF) techniques. A tubular wall thickness of 0.025 mm to 1 mm and a outer diameter (O.D.) of 0.25 mm to 50 mm are most preferred. BaSO4 or other contrast agents can be added to improve the surgeon's vision of the device during delivery, deployment and post-operatively.

Additionally, the construct is useful as a shunt, e.g., in draining fluids from a body cavity such as the brain, or in providing flow between the kidney and the bladder.

EXAMPLES

These are illustrative only, and the invention is not limited thereto.

A homopolymer of p-dioxanone prepared as described, for example, in U.S. Pat. No. 4,838,267, was extruded into a tube using a ¾" extruder (L/D=24) at 110°–160° C. with discharge through 0.38 mm annular die into a water bath at 60° C., followed by a second water bath at 30° C.

The tube was taken up on a spool. The formed tube was 8 mm in outside diameter (O.D.) with a wall thickness of 0.25 mm. Stent 10 of the present invention was then formed by a process wherein the polymer tube was cut into 100 mm lengths. Each 100 mm long tube was then placed on a grooved mandrel where the grooves were 0.3 mm deep with an angle of 15 and spaced apart by 0.3 mm. The tube was then heated at 100° C. and formed into the grooved shape by using a rotating head which forces the tube wall into the depressions on the mandrel. The formed tube was then held in the compressed state for 10 seconds to form the final corrugated shape with a 7.4 mm inner diameter (I.D.) and 8 mm O.D.

For deployment, a typical deployment technique is contemplated to be that a bellows stent 10 prepared as described above, with an initial outside diameter $D_1$, FIG. 2, of 6 mm, is delivered to the site of occlusion in a male urethra via a cystoscope. The tube is then axially compressed when the site is reached, as detected via the cystoscope, to approximate the diameter of the vessel (FIG. 5).

The compression/expansion ability of the construct of the present invention is highly desirable since a balloon catheter or other mechanical assistance is not required to expand the device to the desired shape and diameter, thereby eliminating several steps in the surgical procedure, reducing costs and minimizing damage to the tissue that balloons can often cause during their deployment.

Consequently, the present invention allows for a variety of needs to be met for a wide range of medical applications that would not otherwise be abated by the devices of the prior art. For example, there is a great need for such a device in the urethra to maintain patency following surgical procedures for, e.g., benign prostate hypertrophy. A construct, such as that of the present invention, meets the needs for applications as broad in scope as urethral stents, grafts, and anastomotic couplers.

Therefore, the invention is useful for applications such as stents, grafts, nerve guides and anastomotic couplers.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of delivering and deploying a tubular construct into a body lumen to open occlusions or to provide flow therein, comprising the steps of:

a) inserting a tubular construct comprising a flexible and axially collapsible bellows of a diameter sufficiently less than that of said lumen when axially uncompressed, and greater when axially compressed, into said lumen;

b) advancing said construct through said lumen and around any bends therein to a desired site of deployment; and c) axially compressing at least the bellows of said construct until said bellows achieves a diameter approximately equal to that of said lumen site, so as to be retained at said lumen site.

2. A method of delivering and deploying as defined in claim 1, wherein said step c) comprises the steps of restricting one end of said construct from movement in said lumen while pushing on the other end towards said one restricted end.

3. A method of delivering and deploying as defined in claim 1, wherein said steps a) and b) comprise inserting and moving said tube using a cystoscope.

4. A method of delivering and deploying as defined in claim 2, wherein said steps a) and b) comprise inserting and moving said construct using a catheter.

* * * * *